(12) United States Patent
Chodkowski et al.

(10) Patent No.: US 9,802,017 B2
(45) Date of Patent: Oct. 31, 2017

(54) FACIAL MASK WITH CUSTOM-MANUFACTURED CUSHION ELEMENT, AND ASSOCIATED METHOD

(71) Applicant: KONINKLIJKE PHILIPS N.V., Eindhoven (NL)

(72) Inventors: Lauren Chodkowski, Pittsburgh, PA (US); Maureen Harp, Freedom, PA (US); Kevin Himes, Irwin, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 355 days.

(21) Appl. No.: 14/387,593

(22) PCT Filed: Mar. 22, 2013

(86) PCT No.: PCT/IB2013/052285
§ 371 (c)(1),
(2) Date: Sep. 24, 2014

(87) PCT Pub. No.: WO2013/144797
PCT Pub. Date: Oct. 3, 2013

(65) Prior Publication Data
US 2015/0151066 A1    Jun. 4, 2015

Related U.S. Application Data

(60) Provisional application No. 61/616,134, filed on Mar. 27, 2012.

(51) Int. Cl.
*A61M 16/06* (2006.01)
*A61M 16/08* (2006.01)
(Continued)

(52) U.S. Cl.
CPC ........ *A61M 16/0622* (2014.02); *A61M 16/06* (2013.01); *A61M 16/0611* (2014.02);
(Continued)

(58) Field of Classification Search
CPC combination set(s) only.
See application file for complete search history.

(56) References Cited

U.S. PATENT DOCUMENTS 4,920,580 A * 5/1990 Liff ................... A41G 7/00
2/206
5,072,460 A * 12/1991 Weder ............... A41G 7/00
156/227
(Continued)

FOREIGN PATENT DOCUMENTS

DE    EP 1116492 A2 *  7/2001  ............ A61M 16/06
DE    10138416 A1    2/2003
(Continued)

OTHER PUBLICATIONS

EP 1116492 A2—machine translation.*
(Continued)

*Primary Examiner* — Tan-Uyen (Jackie) T Ho
*Assistant Examiner* — Joseph D Boecker
(74) *Attorney, Agent, or Firm* — Michael W. Haas

(57) ABSTRACT

Disclosed is a method of forming at least a portion of a mask (4) that is structured to engage at least a portion of the face of a patient (52). The method can be generally stated as including employing at least a portion of a data set (74) that is stored on a machine-readable storage medium (72) and that is representative of the shape of at least a portion of the face in generating a configuration for an cushion element (24) of the mask. The cushion element is structured to extend from a support (20) of the mask and to have an engagement end (50) bopposite the support that corresponds with the shape of the at least portion of the face. The method can be generally stated as further including subjecting a workpiece (Continued)

(78) to a formation operation to cause at least a portion of the workpiece to be formed into the cushion element having the engagement end.

14 Claims, 11 Drawing Sheets

(51) Int. Cl.
    *B29C 33/30* (2006.01)
    *A41G 7/00* (2006.01)
    *B29C 43/36* (2006.01)

(52) U.S. Cl.
    CPC .... *A61M 16/0633* (2014.02); *A61M 16/0638* (2014.02); *A61M 16/0683* (2013.01); *A61M 16/08* (2013.01); *A61M 16/0816* (2013.01); *B29C 33/302* (2013.01); *A41G 7/00* (2013.01); *A61M 2016/0661* (2013.01); *A61M 2205/52* (2013.01); *B29C 2043/3623* (2013.01); *Y10S 264/30* (2013.01)

(56) References Cited

U.S. PATENT DOCUMENTS

| | | | | |
|---|---|---|---|---|
| 5,192,560 | A * | 3/1993 | Umetsu | B29C 33/302 249/155 |
| 5,330,343 | A * | 7/1994 | Berteau | B29C 33/302 249/155 |
| 5,796,620 | A * | 8/1998 | Laskowski | B29C 33/302 700/118 |
| 6,098,201 | A * | 8/2000 | Boros, Sr. | A41D 13/1146 2/206 |
| 6,464,924 | B1 * | 10/2002 | Thornton | A61M 16/06 128/206.12 |
| 6,712,072 | B1 * | 3/2004 | Lang | A61M 16/0683 128/206.16 |
| 6,728,589 | B1 | 4/2004 | Delache | |
| 7,054,680 | B1 * | 5/2006 | Genger | A61M 16/00 128/206.21 |
| 7,243,650 | B2 * | 7/2007 | Thornton | A61M 16/06 128/205.25 |
| 7,904,193 | B2 * | 3/2011 | Janbakhsh | A61M 16/06 128/206.21 |
| 7,909,035 | B2 * | 3/2011 | Thornton | A61M 16/0866 128/205.25 |
| 2003/0168063 | A1 * | 9/2003 | Gambone | A61M 16/06 128/203.16 |
| 2005/0199239 | A1 * | 9/2005 | Lang | A61M 16/06 128/206.24 |
| 2005/0284477 | A1 * | 12/2005 | Schrader | A61M 16/0616 128/205.25 |
| 2005/0284478 | A1 * | 12/2005 | Meyer | A61M 16/06 128/205.25 |
| 2006/0137688 | A1 * | 6/2006 | Aisenbrey | A61M 16/06 128/205.25 |
| 2006/0235877 | A1 | 10/2006 | Richard | |
| 2008/0006273 | A1 | 1/2008 | Thornton | |
| 2008/0035158 | A1 | 2/2008 | Pflueger | |
| 2008/0060652 | A1 * | 3/2008 | Selvarajan | A61M 16/06 128/206.21 |
| 2008/0060653 | A1 * | 3/2008 | Hallett | A61M 16/0666 128/206.24 |
| 2008/0078396 | A1 * | 4/2008 | Janbakhsh | A61M 16/06 128/205.25 |
| 2009/0267261 | A1 * | 10/2009 | Mark | A61M 16/06 264/222 |
| 2010/0018534 | A1 | 1/2010 | Veliss | |
| 2010/0065059 | A1 * | 3/2010 | Ho | A61M 16/06 128/206.24 |
| 2010/0147308 | A1 * | 6/2010 | Doshi | A61M 15/08 128/206.24 |
| 2011/0197341 | A1 | 8/2011 | Formica | |
| 2011/0220112 | A1 * | 9/2011 | Connor | A61M 16/06 128/206.24 |
| 2011/0226264 | A1 | 9/2011 | Friedman | |
| 2012/0305003 | A1 * | 12/2012 | Mark | A61M 16/06 128/206.24 |
| 2013/0139824 | A1 * | 6/2013 | Mazzone | A61M 16/06 128/206.21 |
| 2014/0261430 | A1 * | 9/2014 | Davis | A61M 16/06 128/205.25 |
| 2015/0265794 | A1 * | 9/2015 | De Kruyff | A61M 16/06 128/200.23 |

FOREIGN PATENT DOCUMENTS

| | | | | |
|---|---|---|---|---|
| EP | 2295104 A2 | | 3/2011 | |
| FR | 2824739 A1 | | 11/2002 | |
| GB | WO 0059567 A1 | * | 10/2000 | ............ A61M 16/06 |
| WO | WO2011121466 A1 | | 10/2011 | |

OTHER PUBLICATIONS

FR 2824739—machine translation.*
Friedrich K et al.,"On Stamp Forming of Curved and Flexible Geometry Components from Continuous Glass Fiber/Polypropylene Composites", Composites, IPC Business Press Ltd. Haywards Heath, GB, vol. 29, No. 3, Jan. 1, 1998, pp. 217-226, XP004116330.

* cited by examiner

FACIAL MASK WITH CUSTOM-MANUFACTURED CUSHION ELEMENT, AND ASSOCIATED METHOD

CROSS-REFERENCE TO RELATED APPLICATIONS

This patent application claims the benefit under 35 U.S.C. §371 of international patent application no. PCT/IB2013/052285, filed Mar. 22, 2013, which claims the priority benefit under 35 U.S.C. §119(e) of U.S. Provisional Application No. 61/616,134, filed on Mar. 27, 2012, the contents of which are herein incorporated by reference.

BACKGROUND OF THE INVENTION

1. Field of the Invention

The present invention relates generally to a mask that is structured to deliver a flow of breathing gas to a patient, and, more particularly, to such a mask having a custom-manufactured cushion that corresponds with the shape of the face of the patient, and an associated method.

2. Description of the Related Art

There are numerous situations where it is necessary or desirable to deliver a flow of breathable gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder such as sleep apnea syndrome, in particular, obstructive sleep apnea (OSA), or congestive heart failure.

Non-invasive ventilation and pressure support therapies involve the placement of a respiratory patient interface device including a patient interface that is typically secured on the face of a patient by a headgear assembly. The patient interface may be, without limitation, a nasal mask that covers the patient's nose, a nasal cushion having nasal prongs that are received within the patient's nares, a nasal/oral mask that covers the nose and mouth, or full face mask that covers the patient's face. It is known to maintain such devices on the face of a wearer by a headgear having one or more straps adapted to fit over/around the patient's head. Because such respiratory patient interface devices are typically worn for an extended period of time, it is important for the headgear to maintain the patient interface in a desired position while doing so in a manner that is comfortable to the patient.

Such respiratory patient interface devices typically must also form a reliable and generally fluid-tight seal with the face of the patient in the vicinity of the airways in order to ensure that the flow of air is delivered to the airways and does not leak from around the patient interface. Due to the great variability of the facial features of the various patients who require such therapy, reliable seals have sometimes been difficult to provide and/or maintain. While such patient interfaces have typically been available in various sizes, it is understood that any mask of a particular size will have limits with respect to its ability to accommodate facial variability. It thus would be desirable to provide an improved mask that meets these and other limitations known in the relevant art.

SUMMARY OF THE INVENTION

In certain embodiments, the general nature of the invention can be stated as including an improved method of forming at least a portion of a mask that is structured to deliver a flow of breathing gas to the airways of a patient and that is structured to engage at least a portion of the face of the patient in the vicinity of the airways. The method can be generally stated as including employing at least a portion of a data set that is stored on a machine-readable storage medium and that is representative of the shape of at least a portion of the face in generating a configuration for an cushion element of the mask. The cushion element is structured to extend from a support of the mask and to have an engagement end opposite the support that corresponds with the shape of the at least portion of the face. The method can be generally stated as further including subjecting a workpiece to a formation operation to cause at least a portion of the workpiece to be formed into the cushion element having the engagement end.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENT

Figure 1:
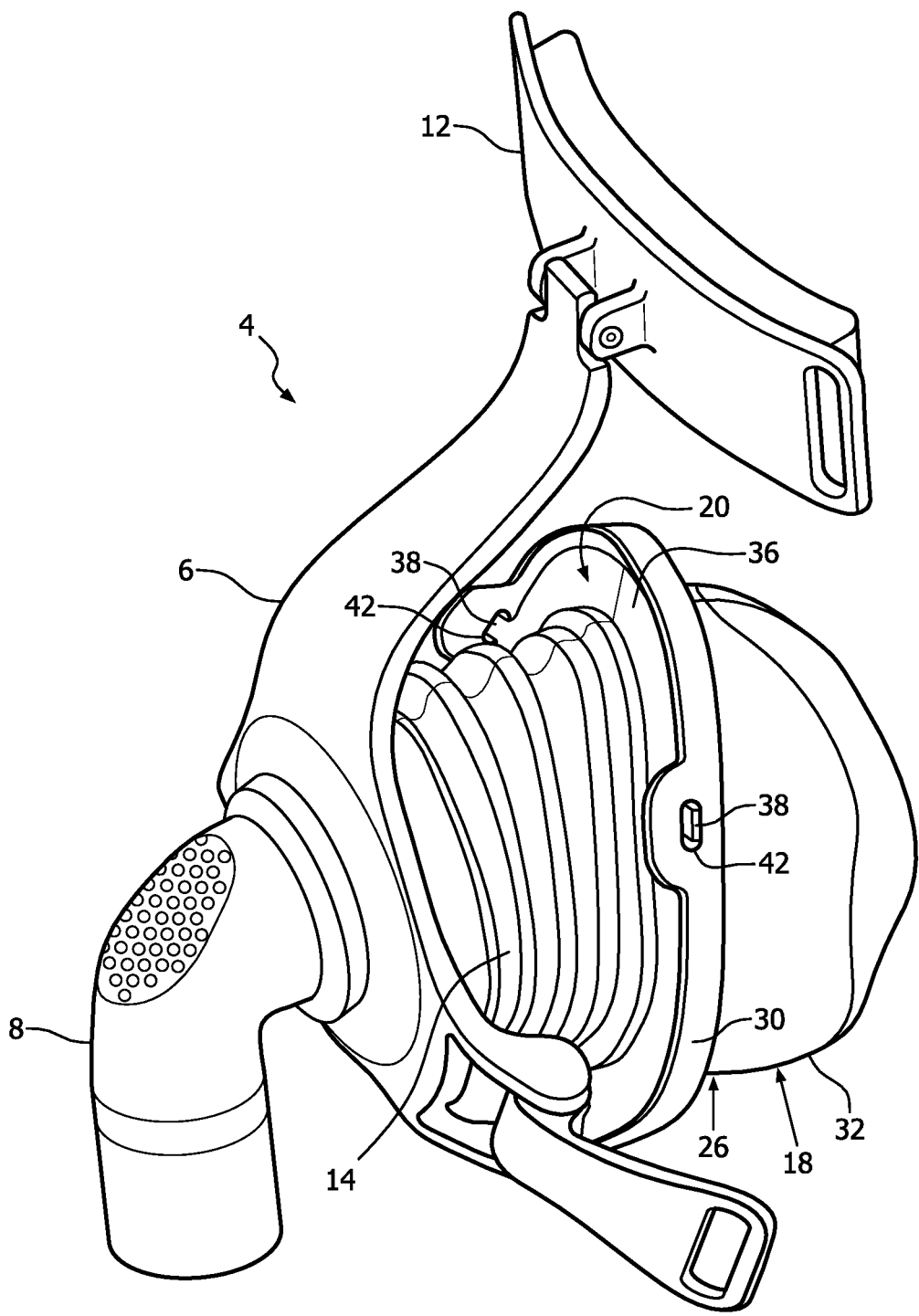
FIG. 1 is a perspective view of an improved mask in accordance with the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

An improved mask 4 in accordance with the present invention is disclosed generally in FIG. 1. As can be generally understood, mask 4 will typically be connected with some type of headgear (not expressly depicted herein) to mount mask 4 to a patient in order to provide a flow of breathing gas to the patient for respiratory therapy. While the depicted exemplary embodiment of mask 4 is of a nasal/oral mask that covers the nose and mouth of a patient, it is noted that the advantageous features of mask 4 that are set forth herein can be employed in any alternative type of patient interface, such as those set forth above, without departing from the present concept.

As will be set forth in greater detail below, mask 4 advantageously includes a custom-manufactured cushion element that has been custom-formed according to a computer-generated configuration which corresponds with the shape of a patient's face. Mask 4 thus maintains a substantially fluid tight seal with the face of the patient without the need to engage mask 4 against the face with a great deal of force, which makes mask 4 relatively more comfortable for the patient to wear as compared with previously known masks.

As can be seen in FIG. 1, mask 4 can be said to include a frame 6 upon which is pivotably disposed an elbow 8 that is connected with a CPAP machine or other source of breathing gas for the provision of respiratory therapy. Mask 4 further includes a forehead brace 12 that is connected with frame 6 and that is engageable with the forehead of the patient. Mask 4 further includes a flexible and collapsible bellows 14 mounted to frame 6 and further includes a patient interface 18 mounted to bellows 14. Elbow 8, bellows 14, and patient interface 18 are in fluid communication with one another and provide a flow of breathing gas to the patient for respiratory therapy. Bellows 14 and patient interface 18 are connected together in any of a variety of fashions that can include adhering, mechanically connecting, co-forming, and the like without limitation.

As suggested above, patient interface 18 is advantageously designed to provide a substantially fluid-tight connection with a patient in order to reliably provide the flow of breathing gases to the patient through the patient's airways. Patient interface 18 itself is depicted in an exploded fashion in FIGS. 2 and 3. It can be seen that patient interface 18 can be said to include a support in the form of a face plate 20, and it further includes a cushion element 24 and a seal apparatus 26 disposed on face plate 20. Patient interface 18 is assembled by receiving a portion of cushion element 24 between a portion of seal apparatus 26 and a portion of face plate 20, and seal apparatus 26 is then mounted to face plate 20. It is noted, however, that in other embodiments of patient interface 18, the various components thereof can be of different configurations and can be connected together in different fashions without departing from the present concept.

Seal apparatus 26 in the depicted exemplary embodiment includes a relatively rigid attachment feature 30 and a relatively flexible and resilient sealing flap 32 that are connected together. In the exemplary embodiment depicted herein, attachment feature 30 and sealing flap 32 are co-formed but could be connected together in other fashions without departing from the present concept. Attachment feature 30 has a plurality of receptacles 42 formed therein for connection with face plate 20.

More specifically, face plate 20 can be said to include a plate member 36 and plurality of protruding tabs 38. When a portion of cushion element 24 is received against a portion of seal apparatus 26, tabs 38 are received in receptacles 42 to cause face plate 20 and seal apparatus 26 to become connected together and to have at least a portion of cushion element 24 interposed therebetween. Patient interface 18 can then be connected with bellows 14 if such connection has not already been made between bellows 14 and face plate 20.

Figure 2:
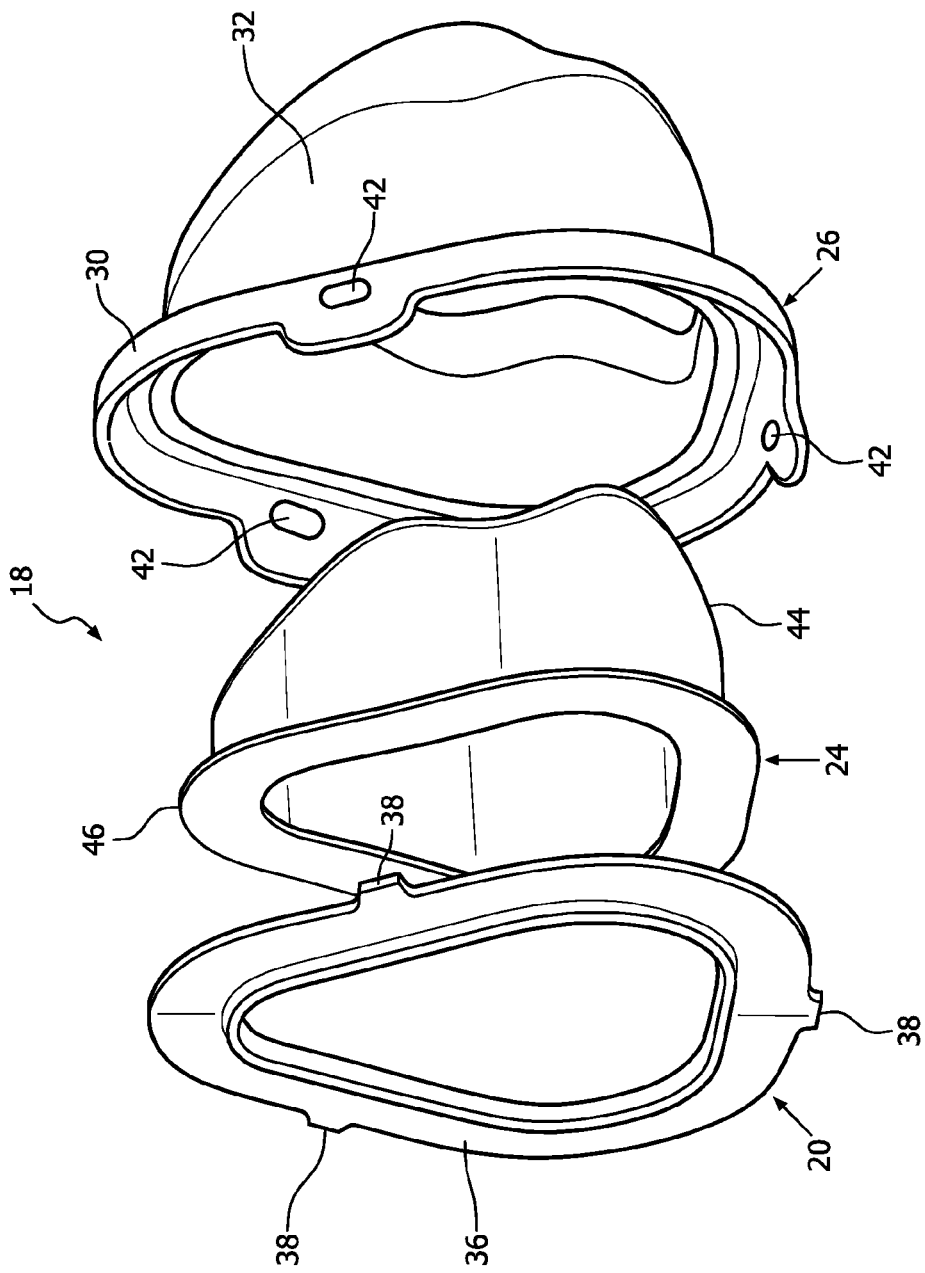
FIG. 2 is an exploded view of a patient interface of the mask of FIG. 1.
Figure 3:
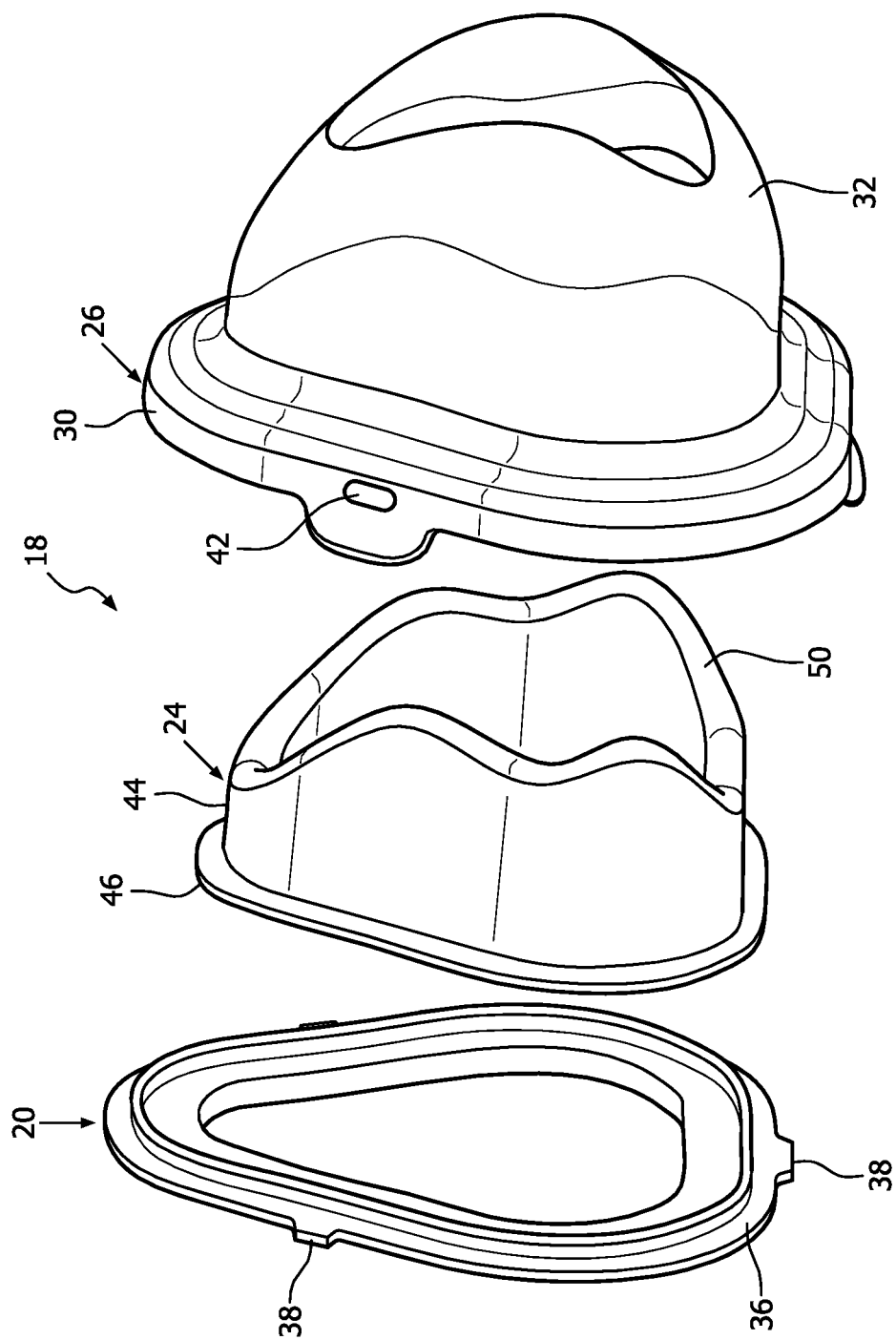
FIG. 3 is another exploded view of a patient interface of the mask of FIG. 1.

As can further be understood from FIGS. 2 and 3, cushion element 24 can be said to include a cushion body 44 that extends in a direction generally away from face plate 20 and to further include a cushion lip 46 that extends in a transverse direction. That is, and as is depicted generally in FIG. 4, whereas cushion body 44 extends in a direction generally away from face plate 20 and toward the face of a patient 52, cushion lip 46 extends in a direction generally parallel with plate member 36 of face plate 20 and is generally the portion of cushion element 24 that is interposed between face plate 20 and seal apparatus 26 and which retains cushion element 24 in position on patient interface 18.

Figure 4:
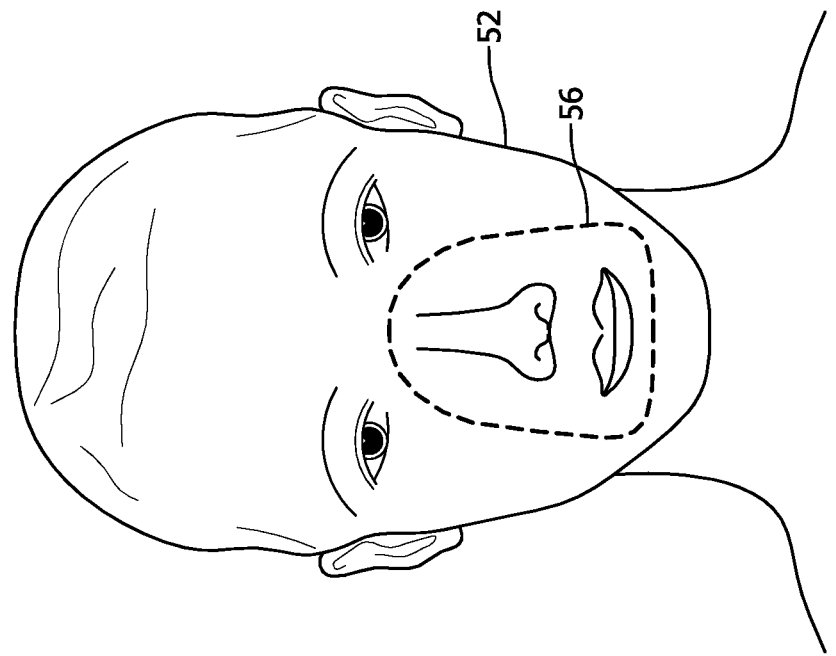
FIG. 4 is a depiction of a cushion element of the mask of FIG. 1 that corresponds with the shape of at least a portion of the face of a patient.
Figure 4:
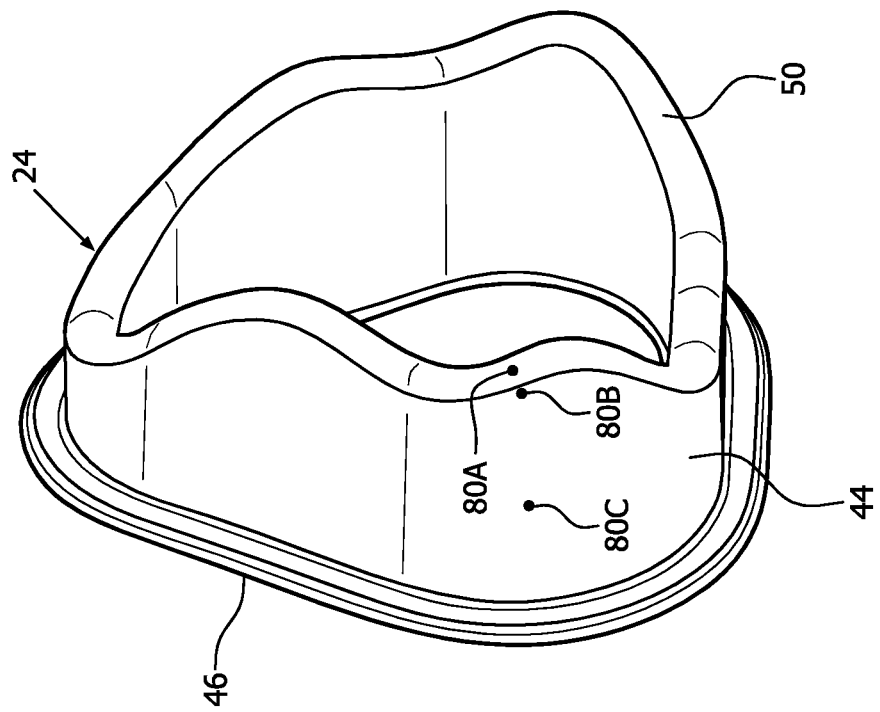

Cushion element 24 can also be said to include an engagement end 50 that is depicted in FIGS. 3 and 4 as being situated on and end of cushion body 44 opposite cushion lip 46. Cushion element 24 and especially engagement end 50 are advantageously custom manufactured according to a computer-generated configuration in order to cause engagement end 50 to be formed in such a fashion that is corresponds with a portion of the face of patient 52. Such custom manufacturing provides improved fit of mask 4 on patient 52 with correspondingly improved comfort and reliability of the seal between mask 4 and patient 52. As will be set forth in greater detail below, cushion element 24 is custom-manufactured to enable patient interface 18 to have a custom fit with the face of patient 52 along an engagement path, such as is indicated with an exemplary dashed line shown generally at the numeral 56 in FIG. 4. It is noted, however, that in patient interface 18 depicted generally herein, the free end of sealing flap 32 opposite attachment feature 30 actually contacts patient 52 along engagement path 56 and is generally interposed between engagement end 50 and patient 52 when mask 4 is installed on patient 52.

With regard to the custom manufacturing of cushion element 24 in accordance with the present invention, it can be generally stated that a computerized device employs the shape of the face of patient 52 to generate a custom configuration for cushion element 24 that will enable patient interface 18 to have a custom fit with the face of patient 52. Variable machinery in employed to manufacture cushion element 24 in accordance with the computer-generated configuration.

Figure 5:
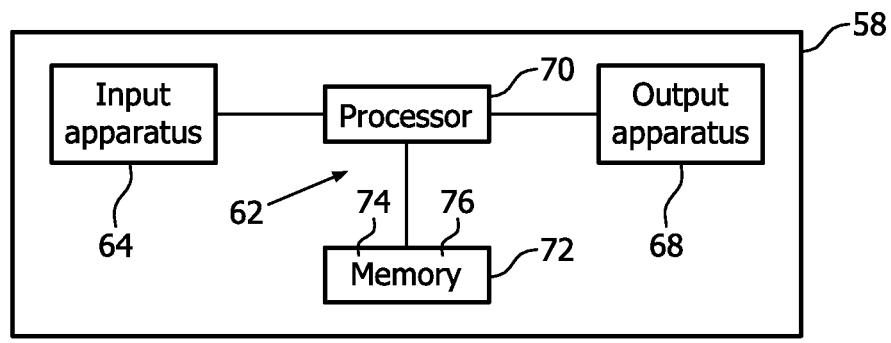
FIG. 5 is a schematic view of a computer upon which at least a portion of an improved method in accordance with the present invention can be performed.

More particularly, FIG. 5 can be said to generally depict a computer 54 having a processor apparatus 62, an input apparatus 64 that provides input signals to processor apparatus 62, and an output apparatus 68 that receives output signals from processor apparatus 62. Input apparatus 64 can include any of a variety of input devices such as scanners, keyboards, and the like, and output apparatus 68 can likewise include any of a variety of output devices such as displays, actuators, and the like, all without limitation. Processor apparatus 62 can be said to generally include a processor 70 and a memory 72. Processor 70 can be any of a wide variety of processors, such as a microprocessor or other type of processor. Memory 72 can be any of a wide variety of machine readable storage media such as RAM, ROM, EPROM, EEPROM, FLASH, and the like without limitation.

Memory 72 has stored therein a data set 74 that is representative of at least a portion of the face of patient 52, and it further has stored therein one or more routines that are indicated generally at the numeral 76. Data set 74 can be obtained in any of a variety of fashions such as by scanning the face of patient 52, by resolution of multiple photographs of the face of patient 52, and the like without limitation. Data set 74 can be in any of a variety of forms such as a plurality of discrete data points, one or more equations that characterize contours of the face, and the like in any combination without limitation.

One of routines 76 employs at least a portion of data set 74 to generate a configuration of cushion element 24 that will enable cushion element 24 to be connected with face plate 20 and seal apparatus 26 in the vicinity of cushion lip 46, and to also correspond with the face of patient 52 along engagement end 50. As such, data set 74 is employed in generating the configuration of engagement end 50 in order to cause it to correspond with the shape of patient 52.

Additionally, however, it is likely desirable to have a plurality of face plates from which face plate 20 is selected. That is, due to the variability of the shapes, sizes, and contours of faces among the population of various patients, it likely will be desirable to provide more than one face plate in order to enable the custom-manufactured cushion element 24 to be configured to have a relatively more customized fit than would be possible with only a single face plate that is configured to work with an entire population. As such, routine 76 will not only generate a configuration for engagement end 50 of cushion element 24, it will also select from a plurality of available face plates the particular face plate 20 that will provide the best fit for patient 52. In this regard, routine 76 may already include data that is representative of the configurations of the available face plates or, even more desirably, will have access to data that is representative of the various face plates that are available and which potentially may change depending upon future availability or non-availability of the various face plates from which face plate 20 is selected.

It thus can be understood that routine 76 employs at least a portion of data set 74, which is representative of the face of patient 52, to custom generate a configuration for cushion element 24 that will enable its engagement end 50 to conform with the face of patient 52 and to enable patient interface 18 to have a substantially fluid-tight seal with the face of patient 52. Routine 76 will also, as appropriate, select from a plurality of face plates the particular face plate 20 that is most appropriate to the face of patient 52 and thus will generate the configuration that not only provides the aforementioned engagement end 50 but that also provides cushion lip 46 and other appropriate portions of cushion element 24 that enable cushion element 24 to cooperate with the selected face plate 20. That is, routine 76 is executed by processor 70 to cause the outputting of the custom-generated configuration for cushion element 24, and the configuration is then employed to custom manufacture cushion element 24.

Cushion element 24 can be manufactured out of any of a wide variety of materials, including metallic and/or non-metallic materials without limitation. In the exemplary embodiment depicted herein, cushion element 24 is formed from a nickel-titanium alloy and further receives a coating of an elastomeric resilient material such as a silicone-based rubber. As is generally understood, nickel-titanium alloys possess super-elastic properties and other properties which can be manifested in a temperature-dependent manner. That is, depending upon temperature, nickel-titanium alloys can have elastic spring characteristics that are linear and/or non-linear. They also can have a shape memory feature. Cushion element 24 can take advantage of such deflection and other characteristics in order to provide a desirable fit with the face of patient 52.

Figure 6:
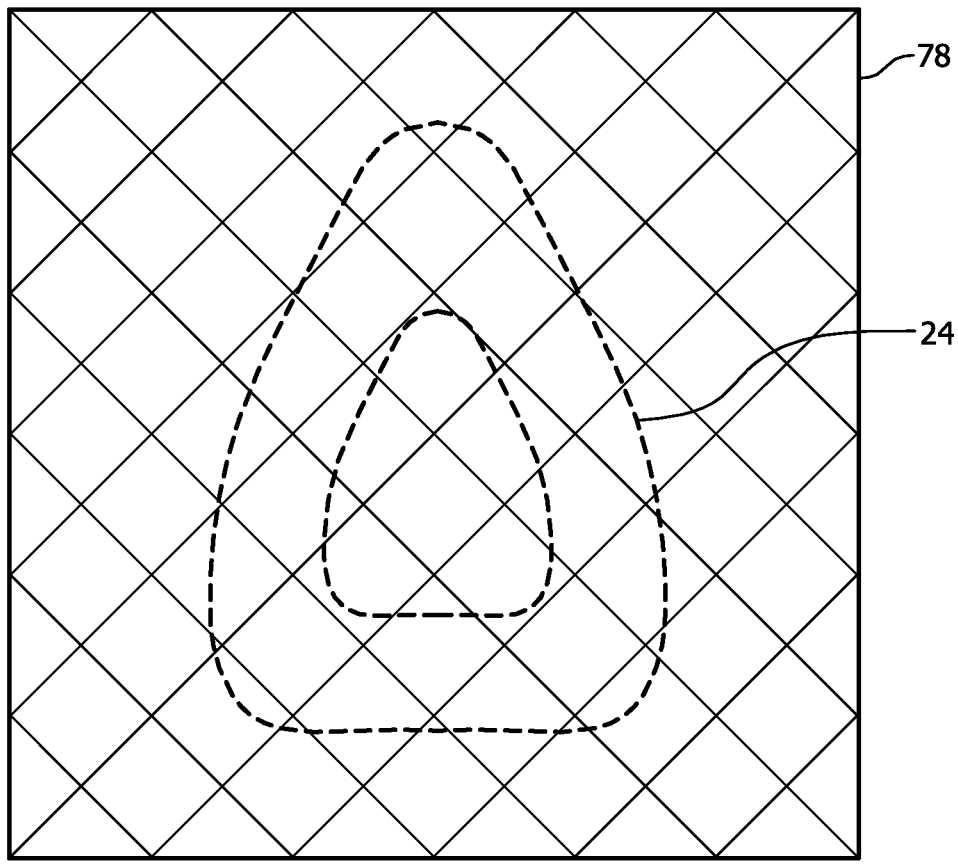
FIG. 6 is a schematic depiction of a workpiece out of which a custom-manufactured cushion element in accordance with the present invention can be manufactured.

In the exemplary embodiment herein, cushion element 24 is formed from a workpiece 78 that is depicted generally in FIG. 6 as being a flat sheet of mesh formed from fibers of nickel-titanium alloy. FIG. 6 also depicts in dashed lines the configuration of cushion element 24 superimposed thereon for purposes of illustration.

More particularly, the present invention employs a variable mold apparatus 82 (FIGS. 7 and 8) that is varied according to the computer-generated configuration of cushion element 24 in order to form cushion element 24 from workpiece 78. The exemplary variable mold apparatus 72 can be said to include a first mold portion 84 and a second mold portion 86 that are each variable according to the configuration and which are compressively engageable with one another to form patient interface 18 out of workpiece 78. More particularly, first mold portion 84 includes a first base member 88 upon which are disposed a plurality of movable mold elements 90. Second mold portion 86 likewise includes a second base member 92 upon which are disposed a plurality of movable mold elements 94. Based upon the configuration for cushion element 24 that has been generated by computer 58, movable mold elements 90 and 94 are positioned on first and second base members 88 and 92, respectively, such that when workpiece 78 is heated and compressively engaged between first and second mold elements 84 and 86, workpiece 78 will be deformed into a shape from which cushion element 24 can be cut.

Figure 7:
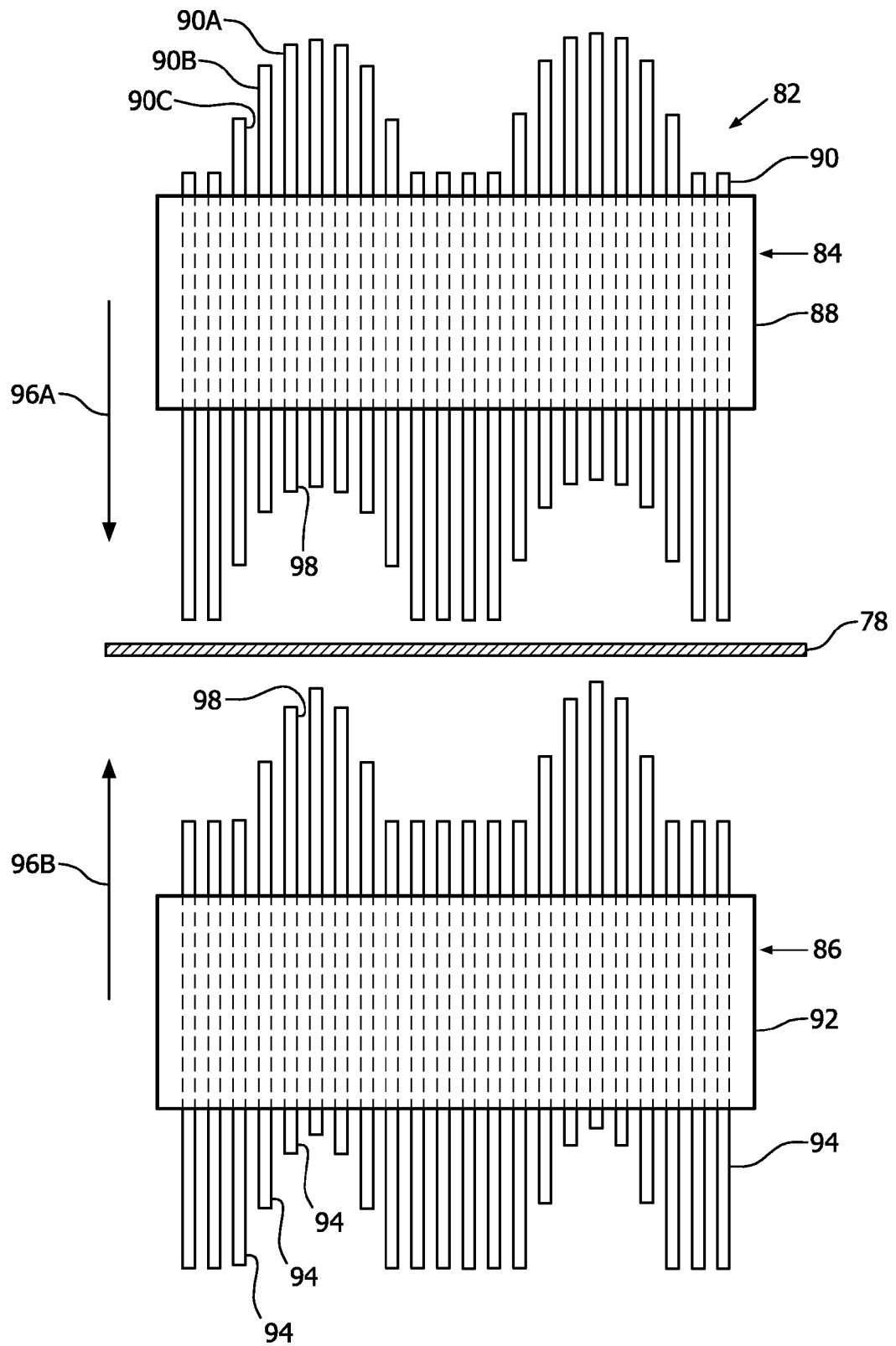
FIG. 7 is a cut away view of a variable mold apparatus that is usable to form the custom-manufactured cushion element out of the workpiece and that has a pair of mold portions that are spaced apart from one another.
Figure 8:
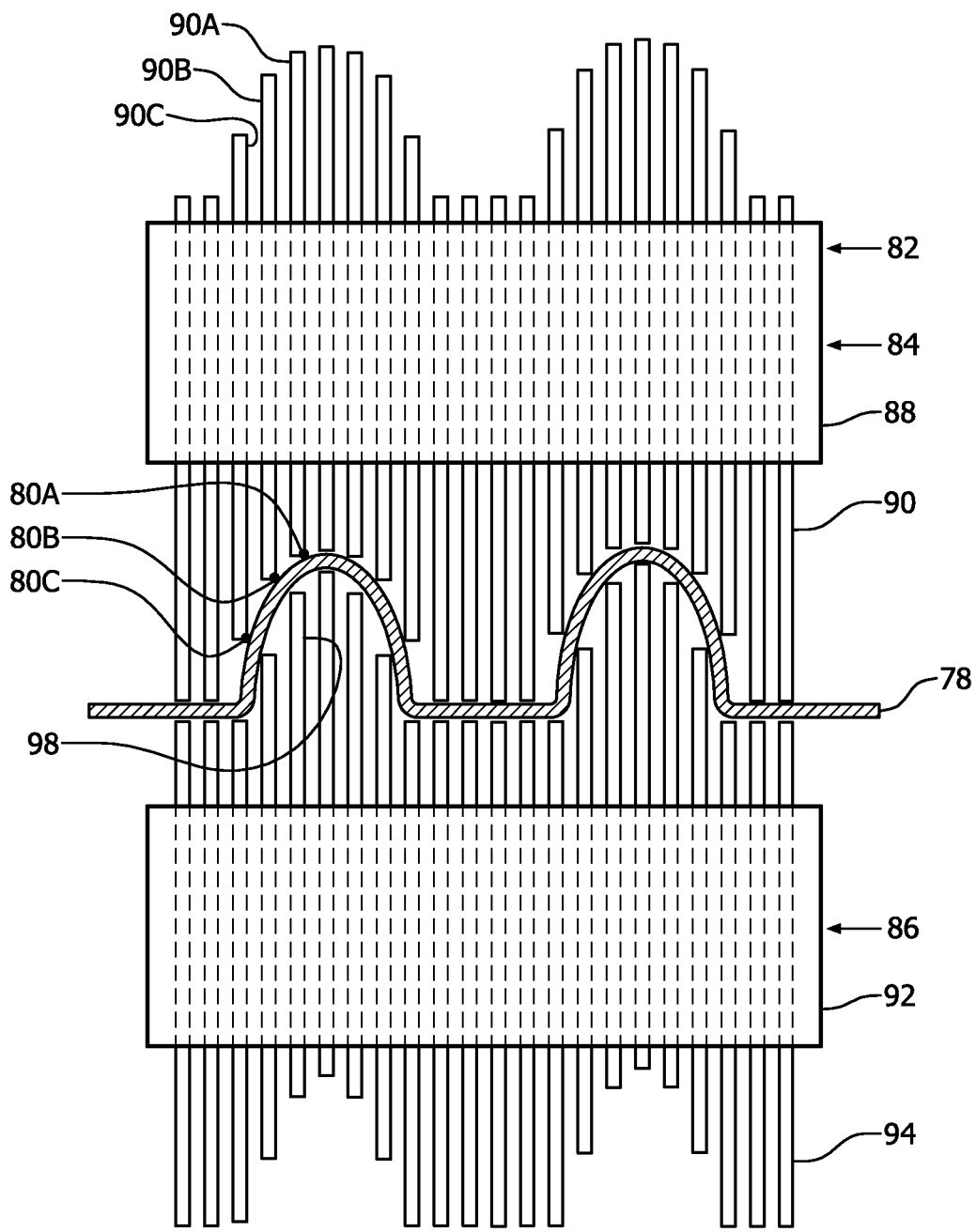
FIG. 8 is a view similar to FIG. 7, except depicting the workpiece compressively engaged between the pair of mold portions.
Figure 9:
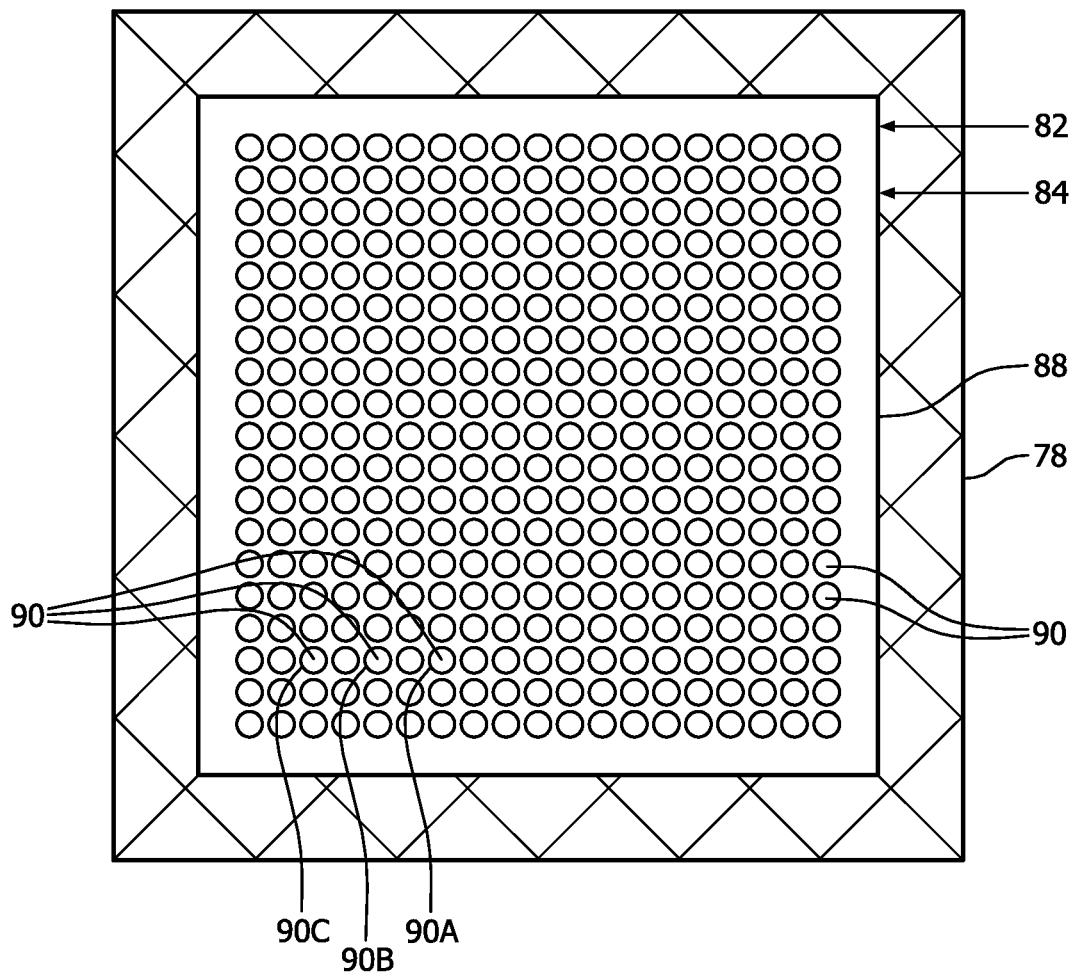
FIG. 9 is a view of a mold portion overlying the workpiece.

In the depicted exemplary embodiment of FIGS. 7-9, movable mold elements 90 and 94 are translatable on first and second base members 88 and 92 such that the ends of movable mold elements 90 and 94 are together situated generally along contours that match the shape of the configuration which cushion element 24 is ultimately desired to have. More particularly, and with regard to movable mold elements 90 of first mold portion 84 which are depicted in FIG. 9 as being superimposed over workpiece 78, each movable mold element 90 can be said to be at a particular location on first mold portion 84. For example, movable mold element 90A is at one location, which is different from the location of movable mold element 90B, and both of which are at a different location than movable mold element 90C.

Moreover, the configuration of cushion element 24 generated by computer 58 from data set 74 has a set of positions in three-dimensional space at each of the aforementioned locations of first mold portion 84. Examples of such positions are the positions 80A, 80B, and 80C. The various movable mold portions 90 are thus translated with respect to first base member 88, as appropriate, along an axis that extends into the plane of the page of FIG. 9 to position the mold elements 90 that are at the various locations (such as at the locations 90A, 90B, and 90C) such that the ends of such movable mold elements 90 that will engage workpiece 78 generally follow the configuration generated by computer 58. Movable mold elements 94 of second mold portion 86 are similarly positioned such that the ends of movable mold elements 94 together form a cooperative mold portion that is cooperative with first mold portion 84.

That is, and as can be understood from FIGS. 7 and 8, movable mold elements 90 and 94 are positioned with respect to first and second base members 88 and 92 such that the ends of movable mold elements 90 and 94 that will contact workpiece 78 are collectively of a contour which, after deformation of workpiece 78, will result in workpiece 78 taking the shape of cushion element 24. While movable mold elements 90 and 94 are depicted herein as being translatable with respect to first and second base members 88 and 92, it is understood that movable mold elements 90 and 94 in other embodiments could be otherwise movable, such as by rotation or otherwise, to be positioned as set forth above in a such fashion that will result in the formation of cushion element 24.

Variable mold apparatus 82 is depicted herein in a schematic fashion in order to illustrate its ability to be custom figured in accordance with the configuration generated by computer 58, and it is understood that movable mold elements 90 and 94 can be positioned in any of a variety of fashions. For example, movable mold elements 90 and 94 can be positioned by actuators, such as mechanical or hydraulic actuators, that are a part of output apparatus 68 and which are operated according to the configuration generated by computer 58. Alternatively, movable mold elements 90 and 94 could be positioned manually in accordance with data values that may be output by computer 58, with a separate data value corresponding with each of the locations of movable mold elements 90 and 94, by way of example. Other fashions of positioning movable mold elements 90 and 94 in accordance with the generated configuration will be apparent. After such positioning, movable mold elements 90 and 94 may need to be locked in position with respect to first and second base members 88 and 92, as appropriate.

In the exemplary embodiment of the method depicted herein, first and second mold portions 84 and 86 are first configured with their movable mold elements 90 and 94 positioned according to the configuration generated by computer 58. Workpiece 78 is then heated and is situated between first and second mold portions 84 and 86, which are then pressed together as is indicated generally with a pair of arrows 96A and 96B for purposes of illustration in FIG. 8. It is understood that one of first and second mold elements 84 and 86 likely will remain stationary and the other pushed generally toward it into compressive engagement therewith.

During such compressive engagement between movable mold elements 90 and movable mold elements 94, individual corresponding pairs of movable mold elements 90 and 94 can be said to form cooperative pairs 98 of movable mold elements that are generally engaged with one another while having a portion of workpiece 78 compressively engaged therebetween. That is, each of the movable mold elements 90, as are indicated generally in FIG. 9, are situated at a location (as at the locations 90A, 90B, and 90C) on first mold portion 84, and each correspond with a correspondingly positioned movable mold element 94 on second mold portion 86 (which is not expressly depicted in FIG. 9 but would be situated underneath first mold portion 84). The movable mold element 90 at the location 90A together with the movable mold element 94 that is at the same location on second mold portion 86 form a cooperative pair 98 of movable mold elements.

Figure 10:
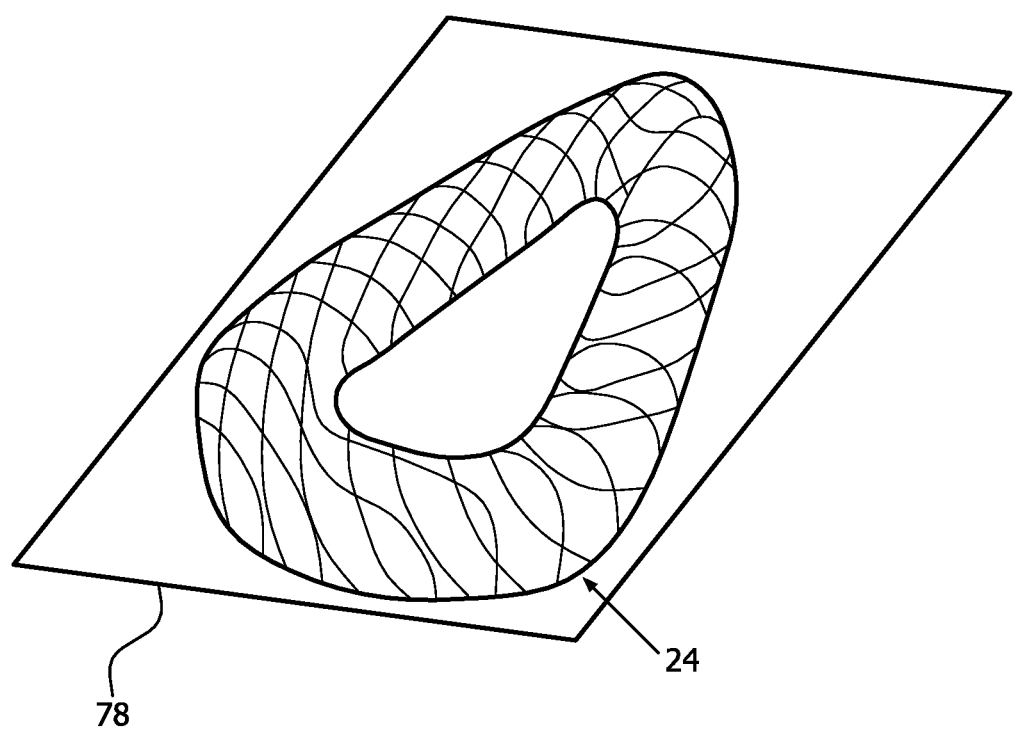
FIG. 10 is a perspective view of the workpiece in a deformed condition and having the cushion element formed therein.
Figure 11:
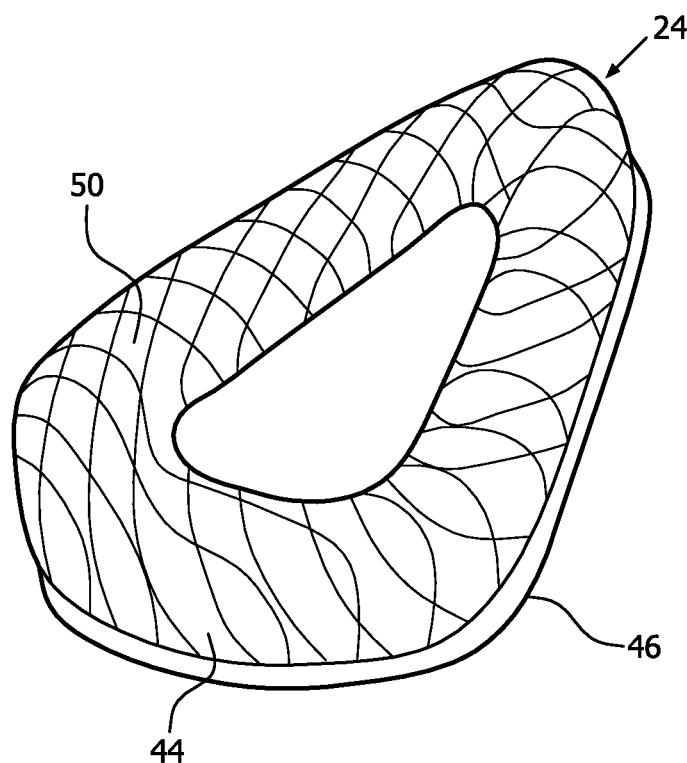
FIG. 11 is a perspective view of the cushion element removed from a remaining portion of the workpiece.
Figure 12:
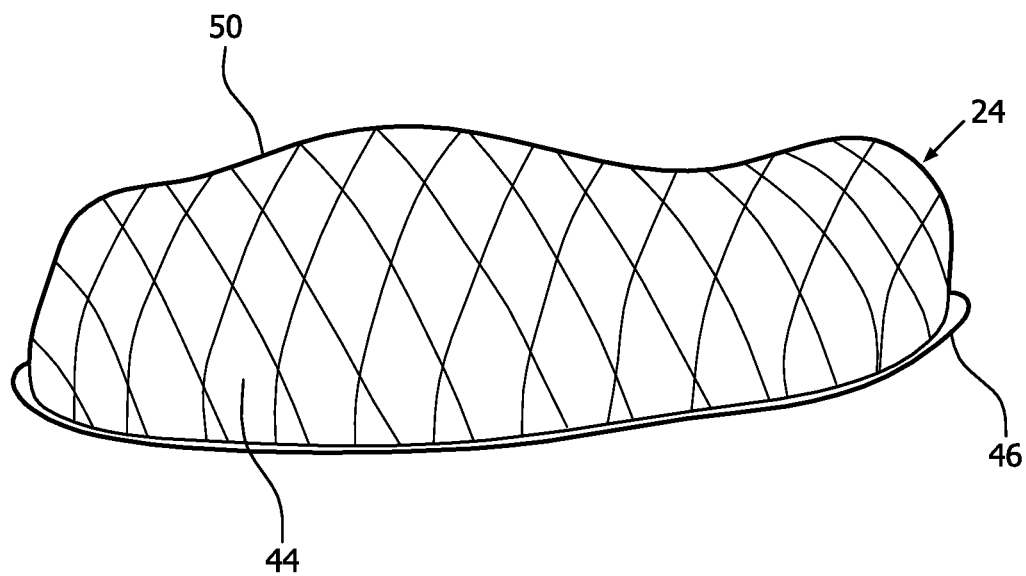
FIG. 12 is a side elevational view of the cushion element of FIG. 11.
Figure 13:
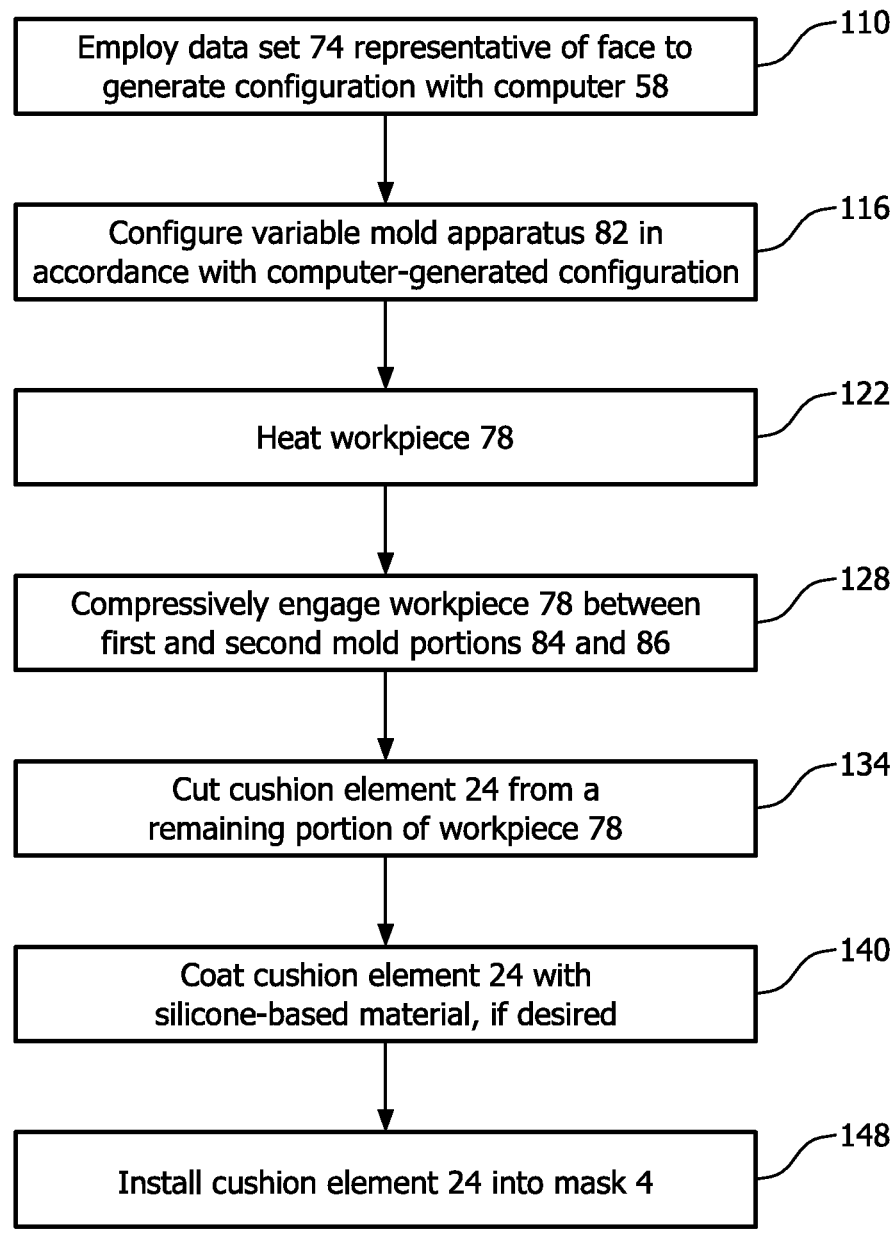
FIG. 13 is a flow chart depicting certain aspects of an improved method in accordance with the disclosed and claimed concept.

The cooperative pairs 98 of movable mold elements at each location thus compressively engage and deform workpiece 78 at the various locations to result in workpiece 78 being deformed as is indicated generally in FIG. 10. That is, FIG. 10 depicts the deformed workpiece 78 having cushion element 24 formed thereon. Cushion element 24 can then be cut from a remaining portion of workpiece 78 and coated with a resilient material, such as a silicone-based elastomer, to result in cushion element 24 as is depicted generally in FIGS. 11 and 12. Cushion element 24 can then be incorporated into patient interface 18 and mask 4 as indicated above.

While the exemplary method is depicted herein as including configuring first and second mold portions 84 and 86 prior to engaging workpiece 78, it is understood that in other embodiments workpiece 78 potentially can be compressively engaged between first and second mold portions 84 and 86, followed by movement of cooperative pairs 78 of movable mold elements in order to deform workpiece 78. In this regard, it is understood that nickel-titanium alloys can be difficult to work, and it is also understood that metallic materials undergoing plastic deformation experience elastic springback that can vary depending upon the properties of the materials out of which workpiece 78 is manufactured. Such properties would be represented by variables within routine 76 in order that the configuration that is generated by computer 58 will result in cushion element 24. Thus, since workpiece 78 will experience at least a certain degree of elastic springback once the compressive forces from first and second mold portions 84 and 86 are removed, the configuration that is generated by computer 58 will typically not be exactly that of cushion element 24 but will be the configuration of variable mold apparatus 82 which will result in cushion element 24 after the formation process set forth above. Thus, while the "configuration" that is generated by computer 58 is described herein as being that of cushion element 24, it is noted that such "configuration" can variously refer without limitation either specifically to cushion element 24 or to the positioning of the various elements of variable mold apparatus 84 from which cushion element 24 is formed.

FIG. 15 depicts an exemplary flowchart which illustrates certain aspects of an improved method in accordance with the disclosed and claimed concept. Processing can be said to begin by employing, as at 110, data set 74, which is representative of the face patient 52, in order to generate a configuration for cushion element 24 or that will result in cushion element 24 when subjected to the formation operation described herein. While data set 74 is assumed herein to already exist, its generation may be considered to be a step that occurs prior to step 110. Movable mold elements 90 and 94 of variable mold apparatus 82 are then positioned, as at 116, in accordance with the configuration generated by computer 58. Workpiece 78 is heated, as at 122, and is compressively engaged, as at 128, between first and second mold portions 84 and 86.

After the deformed workpiece 78 has been removed from variable mold apparatus 82, cushion element 24 is cut, as at 134, from a remaining portion of workpiece 78. Cushion element 24 can then be coated, as at 140, with a silicone coating or other coating, if desired. Cushion element 24 can then be assembled into mask 4, as at 148.

The improved method described herein and the improved custom-manufactured cushion element 24 that is formed from the improved method advantageously provide an improved fit and improved comfort for patient 52. Other benefits will be apparent to those of ordinary skill in the relevant art.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of forming at least a portion of a mask that is structured to deliver a flow of breathing gas to the airways of a patient and that is structured to engage at least a portion of the face of the patient in the vicinity of the airways, the method comprising:
    employing at least a portion of a data set that is stored on a machine-readable storage medium and that is representative of the shape of at least a portion of the face in generating a configuration for a cushion element of the mask, the cushion element being structured to extend from a support of the mask and to have an engagement end opposite the support that corresponds with the shape of the at least portion of the face;
    subjecting a workpiece that is in the form of a flat sheet of mesh which is formed at least in part of metallic fibers to a heating operation that heats the workpiece to at least a predetermined temperature; and
    subjecting the heated workpiece to a formation operation that employs a variable mold apparatus having a plurality of movable mold elements that are positioned in accordance with the configuration and that apply confronting compressive forces to the heated workpiece to cause at least a portion of the heated workpiece to be formed into the cushion element having the engagement end; and
    cutting the workpiece to separate the cushion element from a remaining portion of the workpiece.

2. The method of claim 1, wherein the variable mold apparatus comprises a mold portion having at least a first movable mold element of the plurality of movable mold elements at a first location thereon, and further comprising performing a mold configuration operation that comprises positioning the at least first movable mold element according to a portion of the configuration that corresponds with the location.

3. The method of claim 2, wherein the variable mold apparatus comprises another mold portion having at least a first movable mold element of the plurality of movable mold elements at a first location thereon, and wherein the formation operation comprises engaging the heated workpiece between the mold portion and the another mold portion.

4. The method of claim 3, wherein the at least first movable mold element of the mold portion and the at least first movable mold element of the another mold portion are a cooperative pair of movable mold elements which at least partially confront one another during at least a portion of the formation operation, and wherein the engaging of the heated workpiece between the mold portion and the another mold portion comprises:
    compressively engaging a portion of the workpiece between the cooperative pair of movable mold elements; and
    deforming the portion of the workpiece to conform it with the portion of the configuration that corresponds with the location.

5. The method of claim 4 wherein the mold configuration operation further comprises positioning the at least first movable mold element of the another mold portion according to the portion of the configuration that corresponds with the location.

6. The method of claim 4 wherein the plurality of movable mold elements are situated on each of the mold portion and the another mold portion and together form a plurality of cooperative pairs of movable mold elements, each cooperative pair of movable mold elements corresponding with a separate location on the variable mold apparatus, and wherein the mold configuration operation further comprises positioning each cooperative pair of movable mold elements according to a portion of the configuration that corresponds with each such separate location.

7. The method of claim 6, further comprising performing the mold configuration operation prior to the engaging of the workpiece between the mold portion and the another mold portion.

8. The method of claim 3 wherein the pressing operation further comprises: translating at least one of the mold portion and the another mold portion toward the other of the mold portion and the another mold portion with the heated workpiece situated therebetween; and compressively engaging together the mold portion and the another mold portion with at least a portion of the heated workpiece therebetween.

9. The method of claim 1 wherein the support is one of a plurality of available supports, and further comprising:
    employing at least a portion of the data set to select the support from among the plurality of available supports; and
    employing the shape of the support in the generating of the configuration for the cushion element.

10. The method of claim 1, further comprising coating the cushion element with a resilient material.

11. A mask comprising a cushion element formed in accordance with the method of claim 1, and further comprising a support, the cushion element and the support being connected together.

12. The mask of claim 11, further comprising a sealing element that is structured to be interposed between the cushion element and the face of the patient.

13. The mask of claim 12 wherein the sealing element extends from the support and surrounds at least a portion of the cushion element.

14. The mask of claim 11 wherein the metallic fibers comprise nickel and titanium.

\* \* \* \* \*